United States Patent [19]
Xu

[11] Patent Number: 5,556,402
[45] Date of Patent: Sep. 17, 1996

[54] NEEDLE HOLDER HAVING ROTATABLE HOLDING MEMBER

[75] Inventor: Zhongren Xu, Kanagawa-ken, Japan

[73] Assignee: Terumo Kabushiki Kaisha, Tokyo, Japan

[21] Appl. No.: 346,309

[22] Filed: Nov. 23, 1994

[30] Foreign Application Priority Data

Nov. 24, 1993 [JP] Japan .................................. 5-317382

[51] Int. Cl.$^6$ .................................................. A61B 17/00
[52] U.S. Cl. ........................ 606/147; 606/144; 606/148; 606/207; 112/169
[58] Field of Search .................................. 606/139, 144, 606/145, 147, 148, 151, 205–208; 112/169, 80.03

[56] References Cited

U.S. PATENT DOCUMENTS

| | | | |
|---|---|---|---|
| 253,209 | 2/1882 | Jones | 606/147 |
| 439,910 | 11/1890 | Truax | 606/147 |
| 453,698 | 6/1891 | Hoeller | 606/147 |
| 2,348,218 | 5/1944 | Karle . | |
| 4,621,640 | 11/1986 | Mulhollan et al. . | |
| 5,275,608 | 1/1994 | Forman et al. | 606/205 |
| 5,282,806 | 2/1994 | Haber et al. | 606/145 |
| 5,308,353 | 5/1994 | Beurrier | 606/144 |
| 5,374,277 | 12/1994 | Hassler | 606/207 |

Primary Examiner—Michael H. Thaler
Assistant Examiner—Jeffrey A. Schmidt
Attorney, Agent, or Firm—Burns, Doane, Swecker & Mathis, LLP

[57] ABSTRACT

A needle holder which is used in laparoscopic surgeries by being inserted into a trocal tube inserted into a body cavity of a patient includes an elongated insertion rod having a tip portion; a holding member provided at the tip portion of the insertion rod for removably holding the needle; position control mechanism operable from the outside of the body for adjusting the position of the needle to be held by the holding member; fixing members for fixing the holding member with respect to the insertion rod at a state that the holding member has been adjusted by the position control mechanism; and switching mechanism for switching the state of the holding member between a first state in which the holding member is adjustable with the position control mechanism and a second state in which the holding member is fixed with respect to the insertion rod by means of the fixing members. The holding member is formed from a pair of pinch members each having a semi-spherical shape. The pinch members are joined together to form a substantially spherical body which is rotatable between the fixing member at the tip portion of the insertion rod, thereby enabling to adjust the position of the needle held between the pinch members easily from the outside of the body by operating the position control mechanism when carrying out the step of piercing body tissue during suturing inside the body cavity.

17 Claims, 11 Drawing Sheets

NEEDLE HOLDER HAVING ROTATABLE HOLDING MEMBER

BACKGROUND

1. Field of the Invention

The present invention relates to a needle holder, and in particular relates to a needle holder for use during laparoscopic surgeries.

2. Description of the Background Art

In recent years, surgical operations such as appendectomies, gall bladder removals and the like have been performed by laparoscopic methods that allow such operations to be carried out without the need to cut open the abdomen. In order to carry out such laparoscopic surgeries, a plurality of tubes known as trocar tubes are inserted into the abdominal cavity. Various instruments are inserted through these trocar tubes, including a camera that allows a surgeon to carry out the operation while viewing a monitor.

In this connection, when tissue is being sutured during surgery, the tip of the suturing needle must pierce the tissue at a right angle. However, since suturing needles have a bent shape, they are difficult to manipulate even during standard surgeries performed under the condition that the abdominal cavity is cut open. In particular, when such needles are used during laparoscopic surgeries, they are held by forceps that must be passed through long, narrow trocar tubes, which makes it very difficult for the forceps to have a large angle. Consequently, it has been difficult to freely adjust the angle of the needle during laparoscopic surgery, and this results in increased surgery time, which in turn leads to higher chances of infection.

SUMMARY OF THE INVENTION

It is an object of the present invention to provide a needle holder that makes it possible to easily adjust the position of a needle being used to carry out suturing inside the body.

In order to achieve the object stated above, the present invention is directed to an improvement of a needle holder which is used mainly in laparoscopic surgeries by being inserted into a trocar tube inserted into a body cavity of a patient. This needle holder comprises an elongated insertion rod having a tip portion; holding means for removably holding the needle, the holding means being provided at the tip portion of the insertion rod; position control means for adjusting the position of the needle to be held by the holding means, the position control means being operable from the outside of the body; fixing means for fixing the holding means with respect to the insertion rod at a state that the holding means has been adjusted by the position control means; and switching means for switching the state of said holding means between a first state in which the holding means is adjustable with the position control means and a second state in which the holding means is fixed with respect to the insertion rod by means of the fixing means.

By using the needle holder according to the present invention when carrying out suturing inside a body cavity, it becomes possible to easily adjust the position of the needle, thereby making it possible to shorten surgery time and carry out reliable suturing with ease.

Preferably, the holding means is composed of a pair of pinch members adapted for pinching or gripping the needle from two opposite sides. Further, each of the pair of pinch members has a substantially half spherical shape so that the pinch members form a roughly spherical shape when brought together. By constructing the holding means as described above, the adjustment of the position of the needle can be carried out with ease, especially in the case where the needle holder is to be passed through a narrow communicating tube such as a trocar tube for operations inside a body cavity. Also, since a single structural element can be manipulated to move in a multiple number of directions, there are fewer working parts, and this results in a lower incidence of mechanical failure. In particular, the incidence of mechanical failure during operation is greatly reduced.

Preferably, the fixing means is composed of a pair of fixing members adapted for clamping the pinch members from both sides thereof, and the switching means is formed from a clamping mechanism for adjusting the clamping force of the fixing members. Each of the fixing members may have a roughly half spherical shaped concave portion, respectively, and the pinch members can be accommodated in the space defied by the concave portions of the fixing members.

Further, preferably, the position control means is adapted to adjust the portion of the needle to be held by said pinch members by rotating said pinch members into at least one direction.

Other objects, structures and advantages of the present invention will become apparent from the following description of the preferred embodiments taken in conjunction with the appended drawings.

DETAILED DESCRIPTION OF THE PREFERRED EMBODIMENTS

Figure 1:
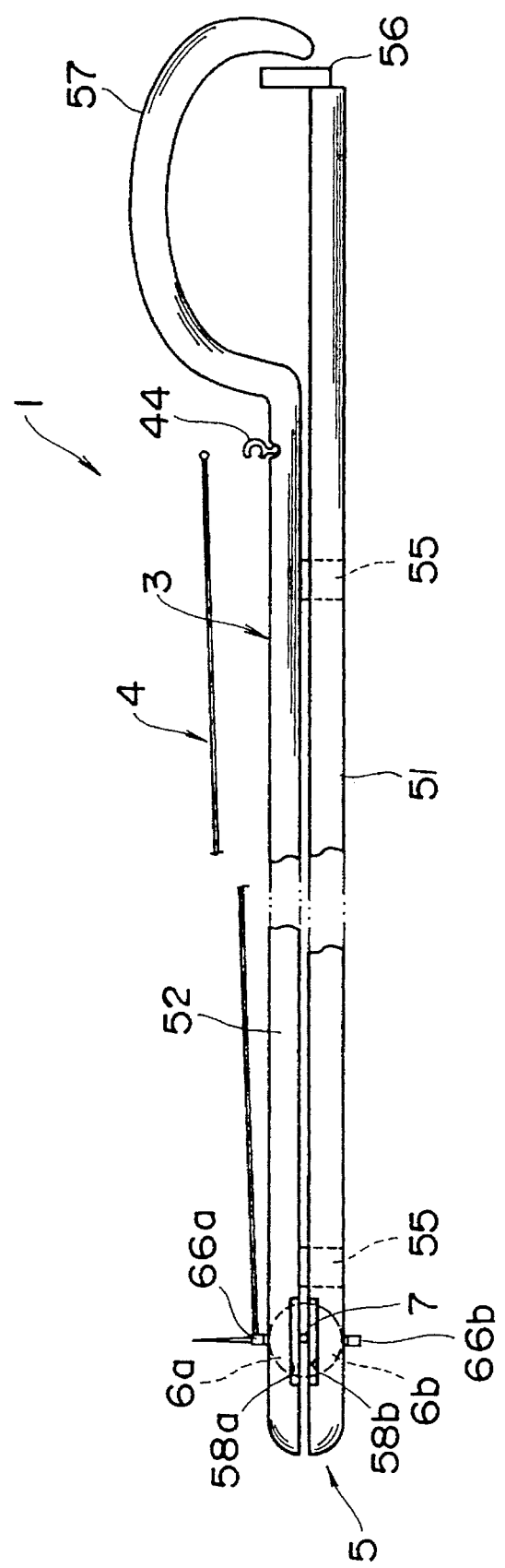
FIG. 1 is a complete side view of a needle holder according to the present invention.

With reference to the drawings, a detailed description of a preferred embodiment for a needle holder according to the present invention will now be given below. In this connection, FIG. 1 shows a complete side view of the embodiment of the needle holder 1 according to the present invention.

As the needle holder 1 of the present invention is to be used mainly for laparoscopic surgeries, it is constructed as an instrument adapted for passage through the inside of a trocar tube. For that reason, the needle holder 1 is constructed to have an elongated slender shape with a tip portion that holds a needle. The needle held at the tip portion is adjusted into a desired position or posture by remote-controlling the needle from the outside of the body.

Namely, the needle holder 1 according to the present invention has an insertion or operation rod 3 for insertion into a trocar tube, a holding member positioned at the tip portion of the insertion rod 3 for holding a needle 7, and a handle portion 57 provided at the base portion of the insertion rod 3. With this construction, the needle 7 is passed into the body cavity by inserting the insertion rod 3 far enough into the trocar tube so that the tip portion thereof enters into the body cavity.

Furthermore, the needle holder 1 has pinch members 6a, 6b which constitute the holding member provided at the tip of the insertion rod 3, a position control means 4 for controlling the operations of the holding member from the outside of the body, a fixing means 5 for fixing the position or posture of the needle 7 after adjustment with the position control means 4, and a clamping mechanism 50 which acts as a means for allowing the needle 7 to be switched from a fixed condition to a condition that permits adjustment of the position or posture of the needle 7.

Figure 2:
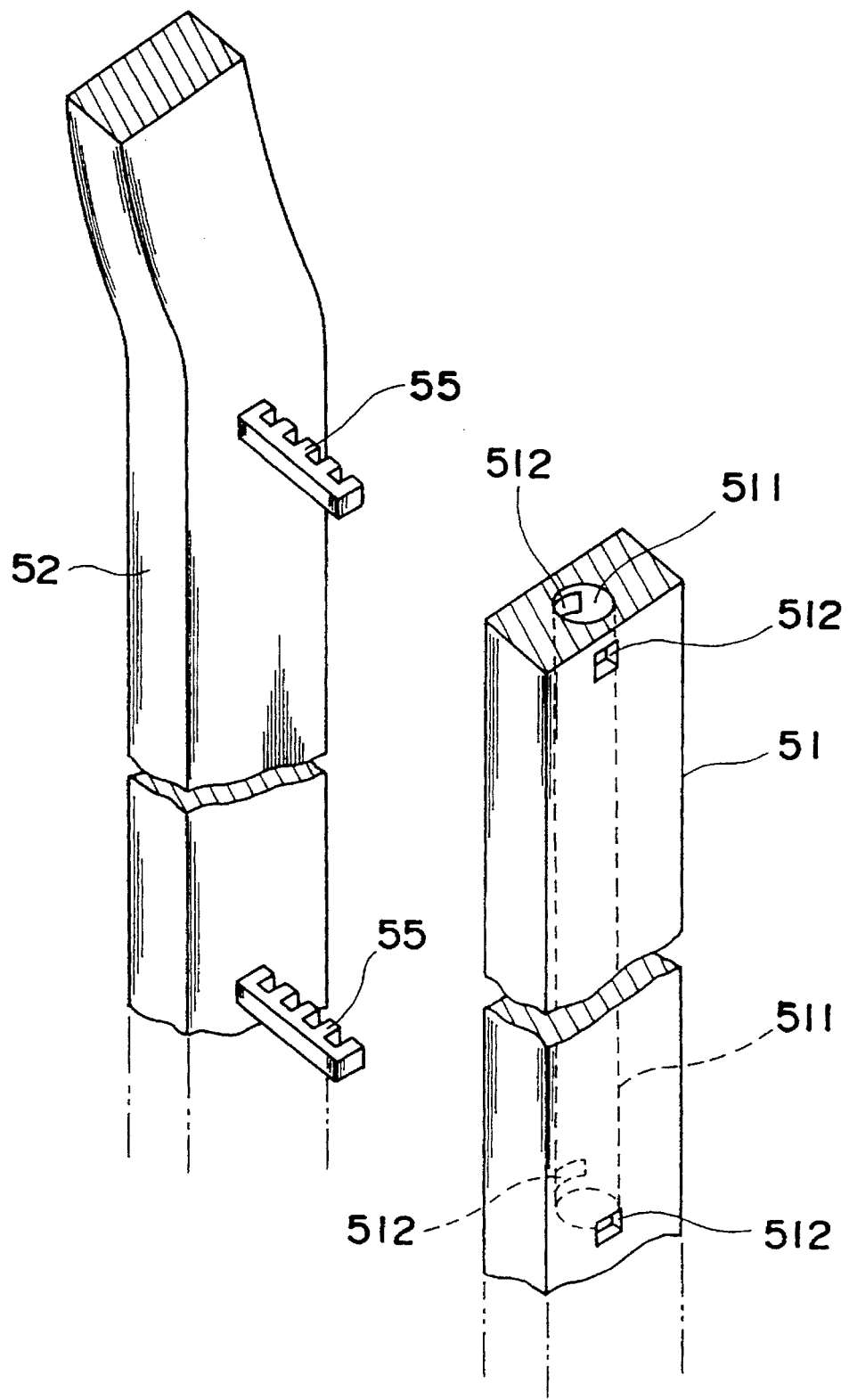
FIG. 2 is a partial perspective view showing the structure of the fixing members.

The fixing means 5 is composed of two fixing members 51, 52 which form the insertion rod 3. As shown in FIG. 2, the bar-shaped fixing members 51, 52 have rectangular cross-sections and are arranged parallel to each other so that thus constructed insertion rod 3 has a roughly square cross section.

Figure 3:
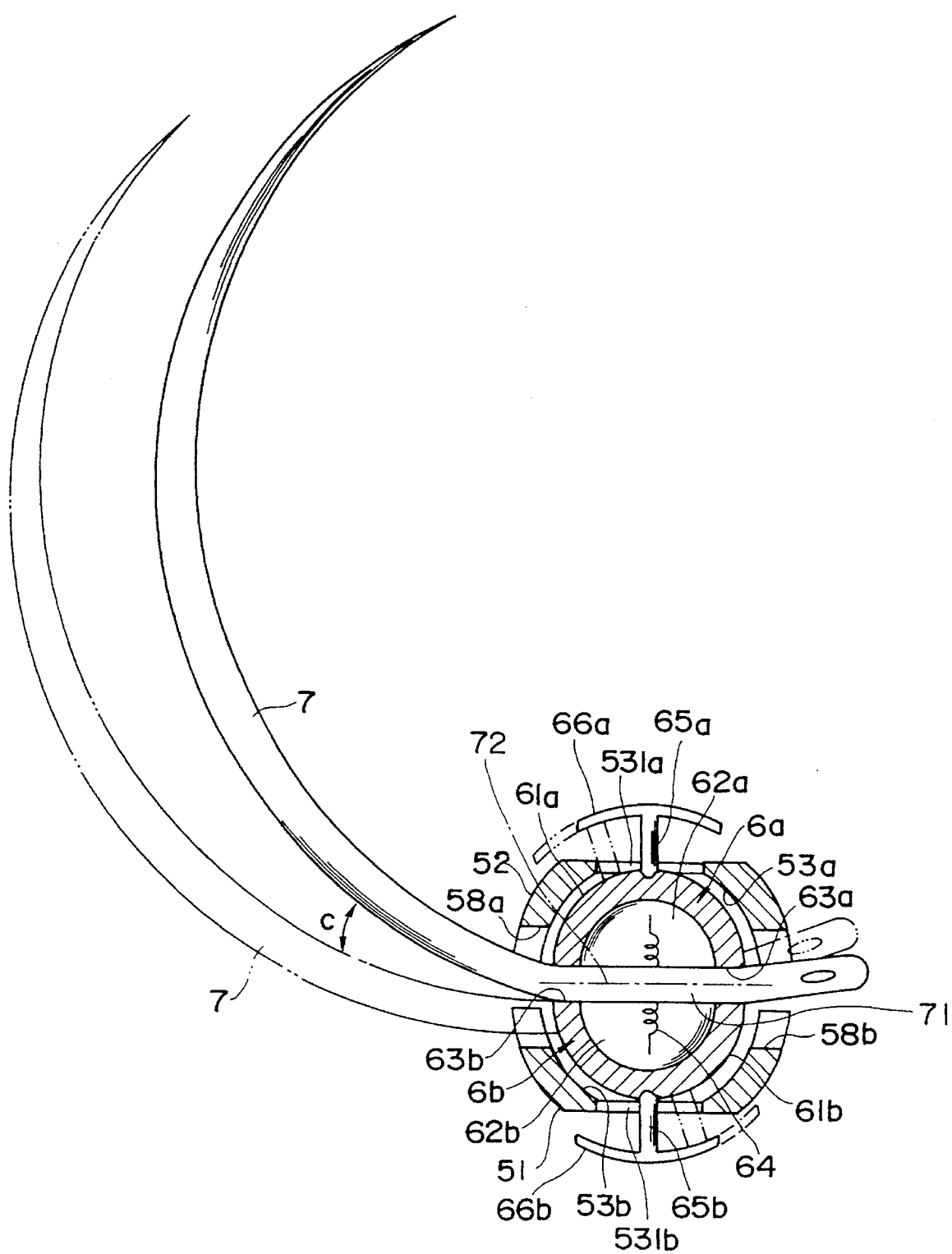
FIG. 3 is a cross-sectional view of the needle holder, which shows a state in which the needle is held between the pinch members clamped by the fixing members.

Now, as shown in FIG. 3, the tip portions of the fixing members 51, 52, which form the tip portion of the insertion rod 3, have a semi-circular cross section, respectively. These tip portions together form a cylindrical-shaped portion having a roughly circular cross section when the fixing members 51, 52 are arranged together. Furthermore, each of the distal end portions of both fixing members 51, 52 is formed into a rounded shape, respectively, so that when the fixing members 51, 52 are arranged together, the distal end portion of the insertion rod 3 has a semispherical shape.

In each of the tip portions of the fixing members 51, 52, there is formed an accommodating portion 53a, 53b having a substantially semi-spherical concave shape. In the space defined by these accommodating portions 53a, 53b, the pinch members 6a, 6b that constitute the holding member are rotatably accommodated. Formed in the bottom of the respective accommodating portions 53a, 53b are holes 531a, 531b, respectively. Furthermore, in the opposite side surfaces of each of the fixing members 51, 52 at the position where the accommodating portion 53a, 53b is formed, there are formed cut out portions 58a, 58b, respectively. As shown in FIG. 1, these cut out portions 58a, 58b form rectangular spaces at the opposite sides of the insertion rod 3, respectively, which allow pivotal movement of the needle 7 held by the pinch members 6a, 6b.

Now, as for the pinch members 6a, 6b serving as the holding member, they are formed so as to have, respectively, semi-spherical shaped outer surfaces 61a, 61b and inner concave portions 62a, 62b that have semi-spherical shapes following the curvature of the outer surfaces 61a, 62b, respectively. Furthermore, the circular end surfaces of the pinch members 6a, 6b that lie between the edge of the inner concave portions 62a, 62b and the outer surfaces 61a, 61b form gripping surfaces 63a, 63b for gripping the needle 7. As a result, when the gripping surfaces 63a, 63b are brought together, the pair of pinch members 6a, 6b together form a roughly spherical shape.

Figure 4:
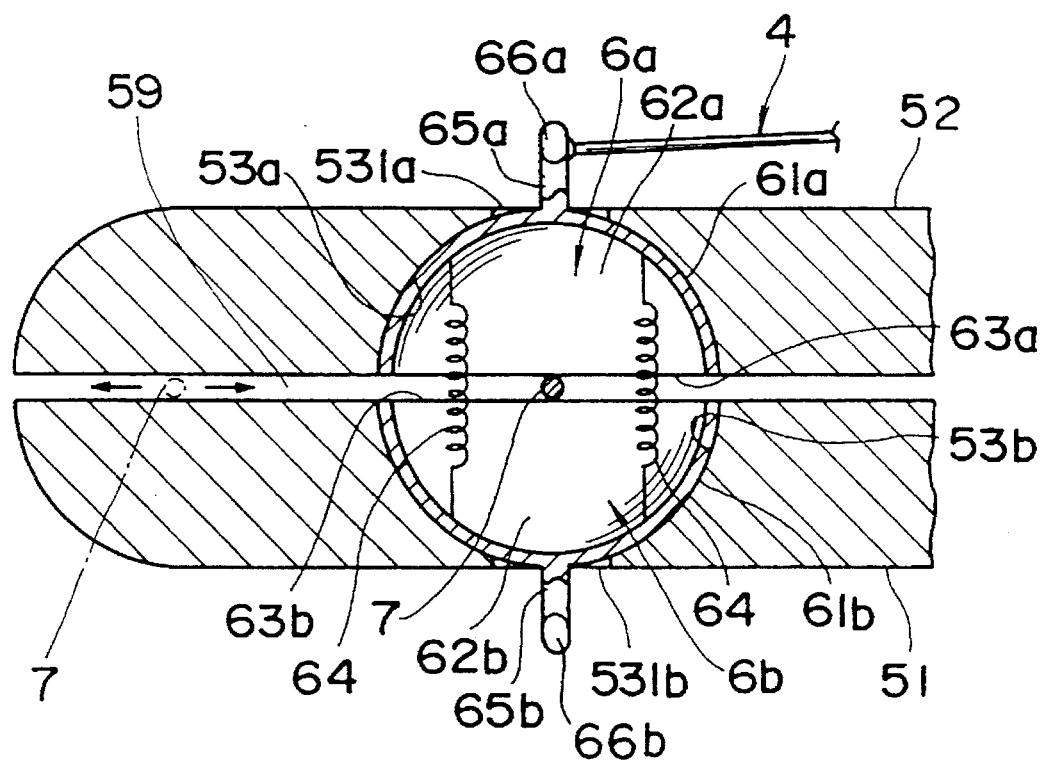
FIG. 4 is a cross-sectional view of the needle holder in the longitudinal direction of the insertion rod, which shows the pinch members, which are in a needle holding state, being fixed in place by the fixing members.
Figure 5:
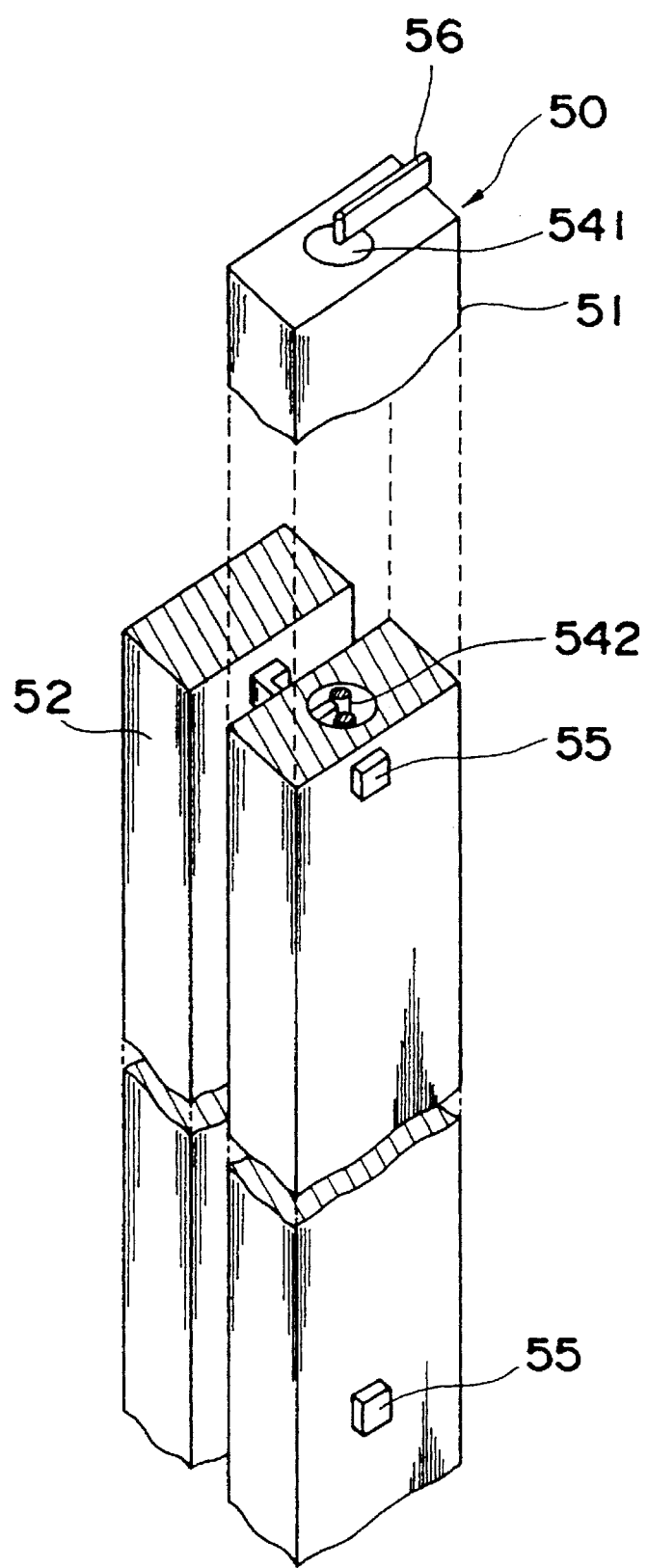
FIG. 5 is a partial perspective view of the fixing members showing the structure of the fixing members and a switching means.

As shown in FIGS. 3 and 4, the pinch members 6a, 6b, in a spherical-like state, are housed inside the accommodating portions 53a, 53b of the fixing members 51, 52. In the present embodiment, the inside surfaces of the accommodating portions 53a, 53b are formed to have semi-spherical shapes so as to make surface contact with the outer surfaces 61a, 61b of the pinch members 6a, 6b.

Furthermore, provided in the inside of the spherical shaped pair of pinch members 6a, 6b are biasing springs 64 which are connected to each of the pinch members 6a, 6b and pass therebetween so as to bias the pinch members 6a, 6b in a direction that pulls them together. By providing the biasing springs in this way, the gripping surfaces 63a, 63b are forced to close in such a way that the circular end surfaces thereof mate with each other, and this enables the pinch members 6a. 6b to join together to form a spherical shape. Thus, the needle 7 is held between the gripping surfaces 63a, 63b by the biasing force of the springs which force the gripping surfaces 63a, 63b toward each other.

Now, as shown in the figures, even though two springs 64 are provided, it is possible to arrange one spring having a high elasticity coefficient instead of the two springs. Further, it is also possible to arrange two springs in a plane that is parallel to the axial direction of the base portion 71 of the needle in a similar construction as described above. (The base portion 71 means a portion of the needle 7 which is to be held by the pinch members.) In this case, it is preferred that both springs be mounted a slight distance away from the center of the pinch members 6a, 6b in the direction toward the base end of the needle holder 1. In this way, since the needle 7 is held at a position between the springs and the distal end portion of the insertion rod 3, the springs will not become a bar when the needle 7 is removed. Namely, the needle 7 can be moved in the axial direction of the insertion rod 3 to pass through the space 59 between the fixing members 51, 52, thereby making it possible to easily remove the needle 7 from the tip portion of the insertion rod 3. As for the biasing member, it is possible to use other elements besides springs, such as elements made from rubber or other elastic materials.

On the central portion of the outer surfaces 61a, 61b of the pinch members 6a, 6b, there are provided pins 65a, 65b, respectively. These pins 65a, 65b pass through the holes 531a, 531b and protrude to the outside of the fixing members 51, 52, respectively. Furthermore, connected to each of the tips of the protruding pins 65a, 65b at right angles thereto, and aligned with the direction of the gripped needle 7, is a side pin 66a, 66b which acts as an engagement portion.

The side pins 66a, 66b are formed so as to have a bent shape that follows the curvature of the outside circumference of the tip portion of the fixing members 51, 52, as seen in a cross section thereof, and are formed so as to have a length that is longer than the diameter of the holes 531a, 531b. By forming the side pins 66a, 66b with such an arc shape, there is a reduced risk of injury to living tissue inside the body cavity when the tip portion of the insertion rod 3 comes into contact with such tissue, or in other words, when the side pins 66a, 66b come into contact with such tissue.

Figure 6:
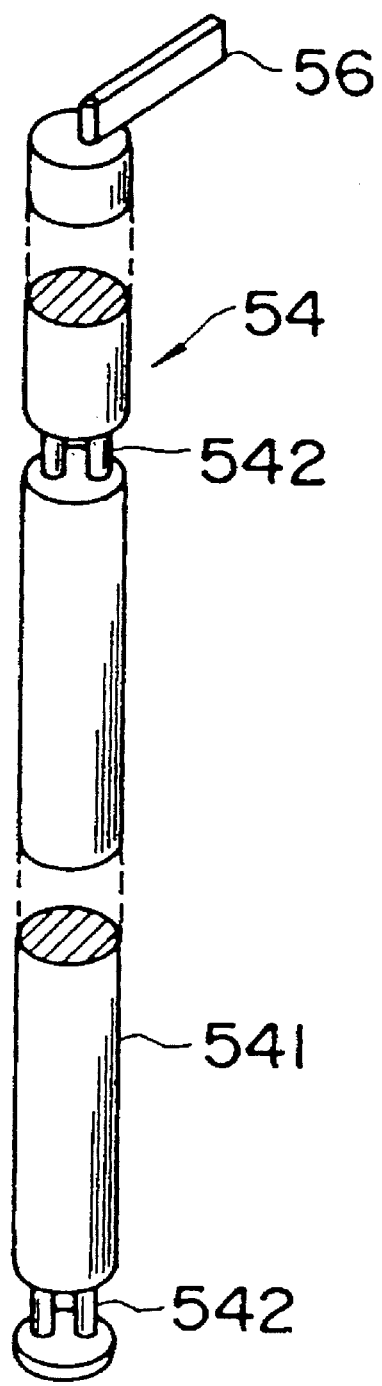
FIG. 6 is a total perspective view of a clamping gear.

Now, as shown in FIGS. 1, 2, 5 and 6, a clamping mechanism 50 which acts as a switching means is provided on the fixing members 51, 52. The clamping mechanism 50 is constructed from a clamping gear member 54, racks 55 which engage with teeth of the clamping gear member 54, and an arm 56 for controlling the rotation of the clamping gear member 54. As shown in FIG. 6, the clamping gear member 54 is constructed by a rotation rod 541 provided with a pair of teeth 542 having a common rotation axis and spaced a prescribed distance apart. Furthermore, the clamping gear member 54 is housed so as to be freely rotatable within a gear housing portion 511 formed in the fixing member 51 in the axial direction thereof.

The racks 55 are provided on the fixing member 52 so as to protrude in a direction towards the fixing member 51 and pass into passages 512 formed through the fixing member 51. The racks 55 are provided at positions that correspond to the positions of the teeth 542 of the clamping gear member 54 housed inside the fixing member 51. Furthermore, the passages 512 are formed through the fixing member 51 at the positions of the teeth 542 of the clamping gear 54 housed in the fixing member 51.

In the above construction, when the fixing members 51, 52 are placed together so as to run parallel to each other, the racks 55 pass into the respective passages 512 and engage with the teeth 542 inside the gear housing portion 511.

The arm 56 is fixed to an end portion of the rotation rod 541 of the clamping gear 54 which protrudes out of the base end of the fixing member 51. By rotating the arm 56, the clamping gear 54 is caused to rotate, and this rotation causes the rack 55 to move due to the engagement between the rack and the teeth, thereby enabling the spacing between the fixing members 51, 52 to be adjusted.

Figure 7:
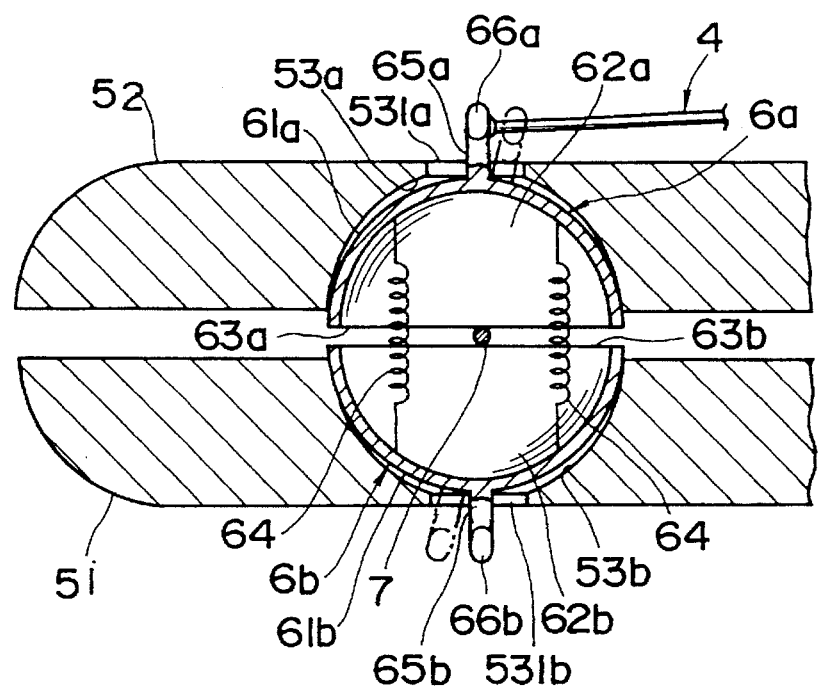
FIG. 7 is a cross-sectional view of the needle holder showing the pinch members, which are in a needle holding state, being held by the fixing members in a way that will enable the position of the pinch members to be adjusted.

According to the above construction, if the arm 56 is rotated and the spacing between the fixing members 51, 52 is enlarged, as shown in FIG. 7, spaces will be created between the pinch members 6a, 6b and the fixing members 51, 52, thereby making it possible for the pinch members to rotate inside the accommodating portions 53a, 53b. In this condition, by rotating the pinch members 6a, 6b, it is possible to change the position or posture of the needle 7 held by the pinch members 6a, 6b.

The range of rotation of the pinch members 6a, 6b within the accommodating portions 53a, 53b is restricted by the size of the holes 531a, 531b through which the pins 65a, 65b are passed. Also, the needle 7 held by the pinch members 6a, 6b is able to move within the rectangular spaces defined by the cut out portions 58a, 58b.

Figure 8:
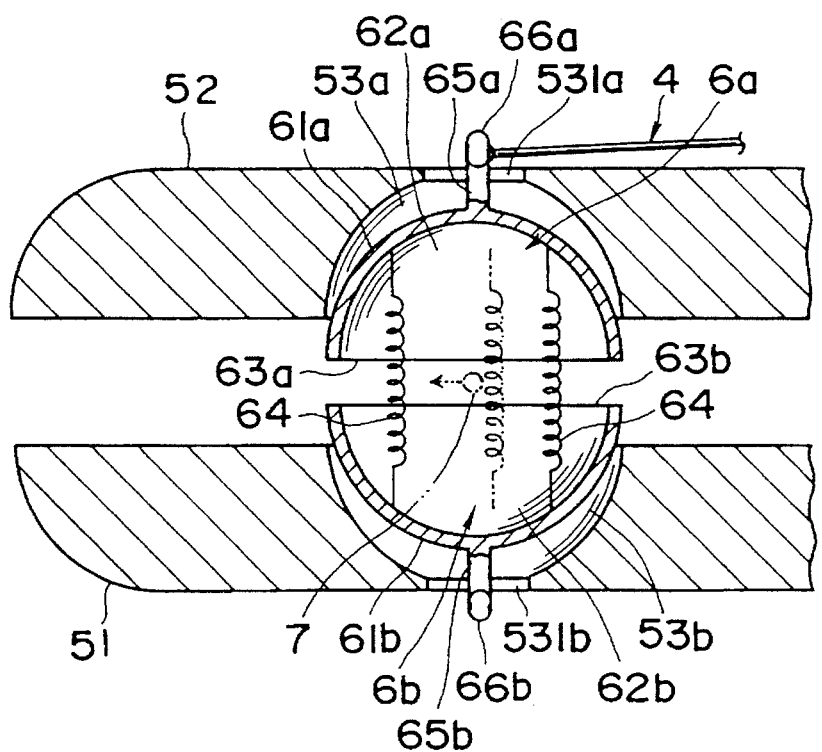
FIG. 8 is a cross-sectional view of the needle holder showing the pinch members being held by the fixing members in a way that will release the grip of the pinch members on the needle.

Moreover, when the arm 56 is further rotated and the spacing between the fixing members 51, 52 is further enlarged, the edges of the holes 531a, 531b engage with the side pins 66a, 66b so as to force the pinch members 6a, 6b to be pulled apart, as shown in FIG. 8. By this action, the grip of the pinch members 6a, 6b on the needle 7 is released, thereby making it possible to remove the needle 7 from the needle holder 1 inside the body cavity along a path that follows the axis 72 of the needle 7.

In the present embodiment, by forming the pinch members 6a, 6b so as to have a spherical shape when joined together, the rotational position of the pinch members 6a, 6b can be easily changed, resulting in a simple construction having relatively few elements, which in turn allows for easy operation. In particular, by having a structure that allows for the rotation of a spherical body, it becomes possible to rotate the held needle 7 easily in any desired direction, thereby enabling the position of the needle 7 to be controlled with ease, which makes this structure suitable for operations through the narrow space such as a trocar tube and the like. Furthermore, because the pinch members are formed into the spherical body, the overall shape of the pinch members that hold the needle 7 remains as it is even when the position of the held needle 7 is changed. As a result, it becomes possible to fix the position of the needle 7 at any desired position with ease by clamping the spherically shaped pinch members with the fixing members 51, 52 at any rotational position thereof.

Figure 9:
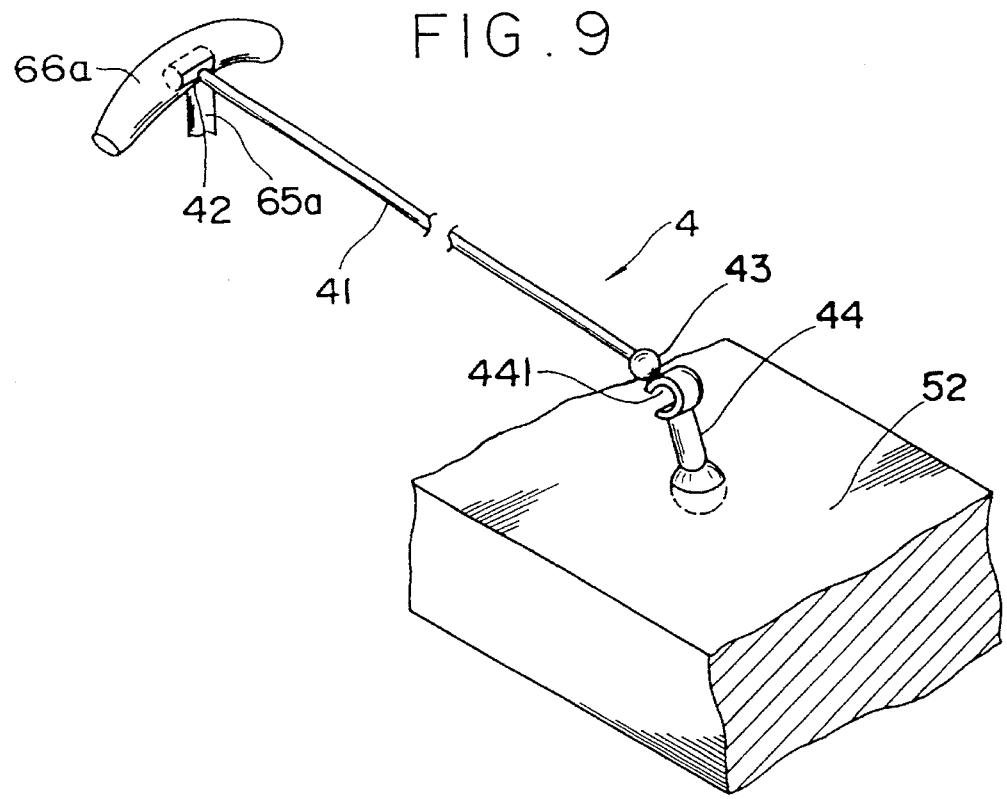
FIG. 9 is a total perspective view of a first embodiment of a position control means according to the present invention.

As shown in FIGS. 1 and 9, the needle holder 1 has a position control means 4 for adjusting the position or posture of the needle 7 by rotating the pinch members 6a, 6b housed within the accommodating portions 53a, 53b. The position control means 4 has an elongated control rod 41. Provided at one end of the control rod 41 is a connection portion 42. The connection portion 42 has a cylindrical shape of which the axis extends perpendicular to the control rod 41. The cylindrical shaped connection portion 42 is received in a concave portion having substantially the same shape and formed in the side pin 66a in such a manner that the control rod 41 can be pivoted with respect to the side pin 66a only in the up and down direction in FIG. 9. As a result, by moving the control rod 41 back and forth along its axial direction and rotating it about the connection portion 42 or a spherically shaped control end portion 43 of the control rod 41, it is possible to rotate the pinch members 6a, 6b in any direction, thereby making it possible to adjust the needle 7 to any desired position.

Provided at the base portion of the fixing member 52 is a receiving holder 44 for receiving and holding the spherically shaped control end portion 43 formed at the other end of the control rod 41. The receiving holder 44 is provided so as to be pivotable in any direction with respect to the fixing member 52. Further, the receiving holder 44 has at a tip portion thereof a spherically shaped concave connection end portion 441, to which the control end portion 43 of the control rod 41 is received at any angle. When the control rod 41 is operated in order to adjust the position of the needle 7, the control end portion 43 is disengaged from the connection end portion 441 if necessary.

By having the above structure, even if the position of the control end portion 43 of the control rod 41 changes when the position of the needle 7 is adjusted, it is possible to follow such changes and change the position where the control end portion 43 is received and held by the receiving holder 44. At the time when the needle holder 1 is being used after the insertion rod 3 has been passed through a trocar tube, the control end portion 43 and the receiving holder 44 are in the outside of the body, thereby making it possible to adjust the position of the needle 7 from the outside of the body.

Figure 10:
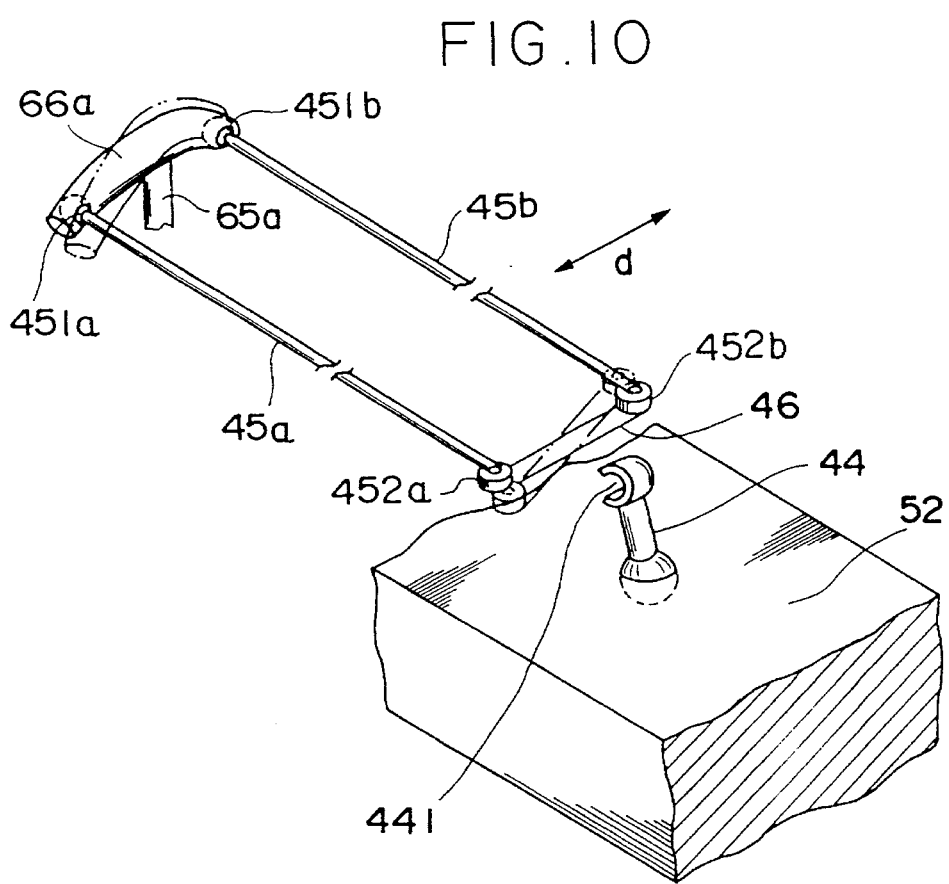
FIG. 10 is a total perspective view of a second embodiment of a position control means according to the present invention.
Figure 11:
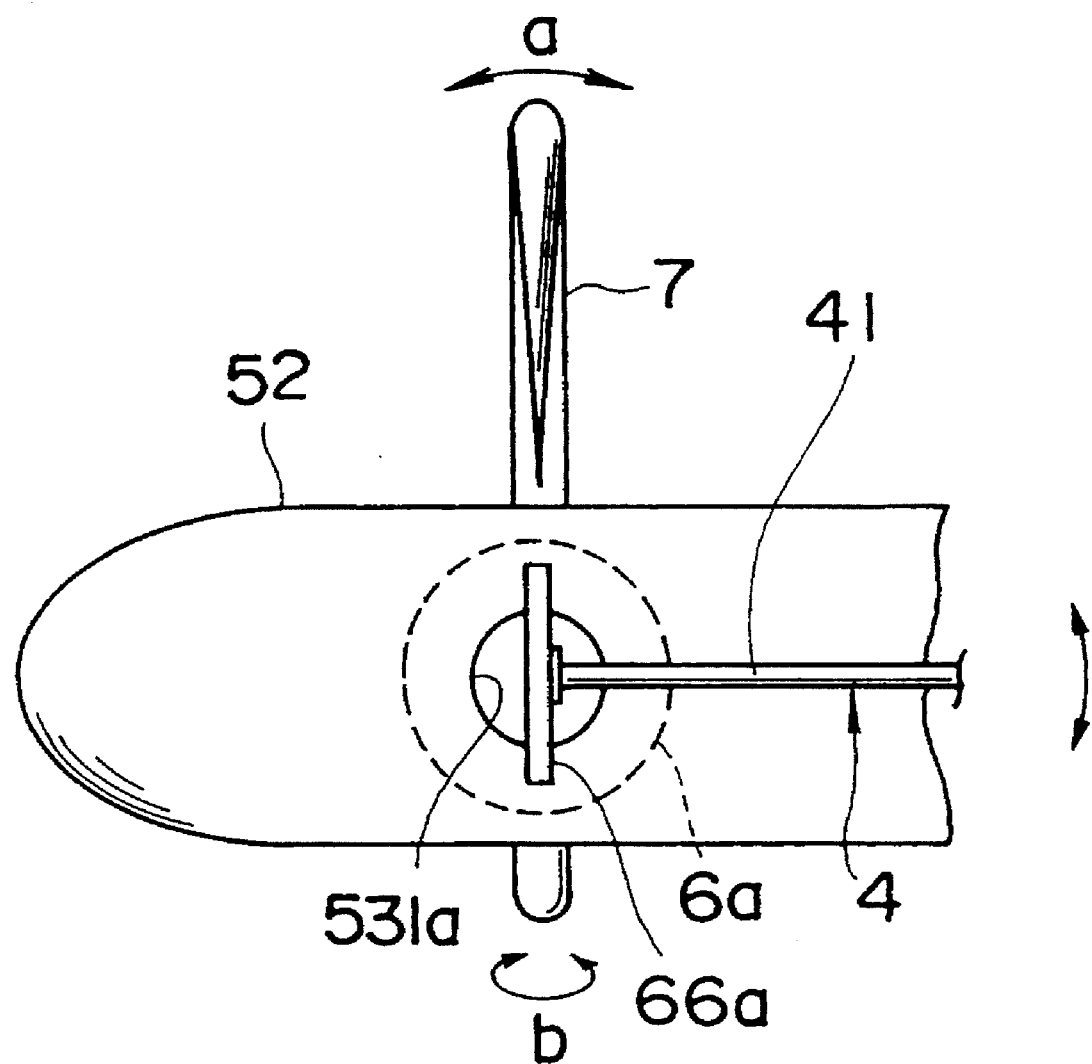
FIG. 11 is a top plan view of the tip portion of the needle holder, which shows the state in which a needle is held by the needle holder.

For the position control means 4 described above, it is also possible to provide the following alternate structure in order to easily carry out control from a control position outside the body. For example, as shown in FIG. 10, it is possible to utilize two control rods 45a, 45b similar to the control rod 41 described above. In this case, the control rods 45a, 45b have spherical connection portions 451a, 451b which are pivotably connected to mating concave portion of the side pin 66a near the end portions thereof, respectively. Furthermore, the control rods 45a, 45b have control end portions 452a, 452b which are connected to a connection rod 46 so as to be freely pivotable thereto, such that the side pin 66a, control rods 45a, 45b and connection rod 46 form a rectangular link structure.

In this structure, by tilting the connection rod 46 from the position indicated by the solid line to the position indicated by the chain line in FIG. 10, the link structure is deformed and therefore the pinch members 6a, 6b are caused to rotate around an axis passing through the center of the pins 65a, 65b. Further, by moving the control rods 45a, 45b along their respective axial directions, the needle 7 is caused to rotate around the axis 72 of the needle 7 that is held by the pinch members 6a, 6b. Furthermore, by moving the control rods 45a, 45b in a sideways direction (indicated by the arrow "d") while being kept parallel to each other, the needle 7 is caused to rotate around the axis of the insertion rod 3. According to this modification, since the holder 44 is mounted to the fixing member 52 in freely pivotal and rotatably manner, it is possible to carry out the adjustment of the position of the needle 7 without removing the connection rod 46 from the connection end portion 441 of the receiving holder 44.

In a manner as described above, the position of the needle 7 can be freely adjusted. In such a case, after the needle 7 has been adjusted to a desired position, the fixing members 51, 52 are used to fix the pinch members 6a, 6b as described above.

Now, an explanation will be given for the use of the needle holder 1 when the suturing needle 7 is to be used to carry out suturing. First, the arm 56 is rotated to enlarge the space between the fixing members 51, 52, causing the edges of the holes 531a, 531b of the fixing members 51, 52 to engage with the side pins 66a, 66b, and this forces the pinch members 6a, 6b to be pulled apart. Next, the base portion 71 of the needle 7 is inserted into the space created between the pinch members 6a, 6b and then the arm 56 is rotated in the opposite direction to reduce the space between the fixing members 51, 52, which causes the fixing members 51, 52 to be brought together until the biasing force of the spring 64 is able to pull the pinch members 6a, 6b together to hold the needle 7 therebetween. Then, after a suturing thread 2 is passed through the needle 7, the tip of the needle holder 1 which holds the needle 7 is passed through a trocar tube to position the needle 7 inside a body cavity.

Next, the needle holder 1 is moved near the site where the needle 7 is to pierce the tissue, and then the position of the needle 7 is adjusted so as to have the tip of the needle 7 pierce the tissue that is to be sutured at a right angle by operating the position control means 4 to rotate the pinch members 6a, 6b in the desired direction of rotation. As shown in FIGS. 3 and 11 through 13, by moving the pins 65a, 65b in one of three directions or in a combination of two or more of the three directions within the range of space permitted by the holes 531a, 531b, it is possible to adjust the position of the needle 7.

Figure 12:
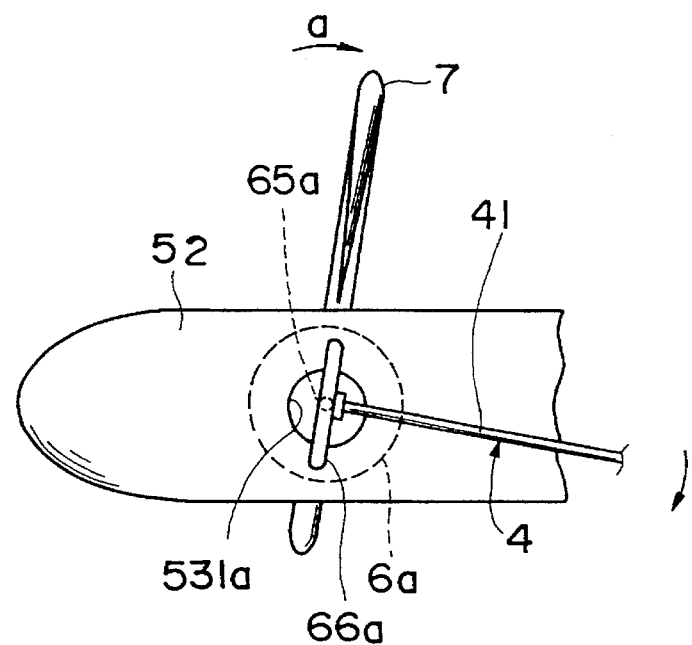
FIG. 12 is a top plan view of the tip portion of the needle holder, which shows the state in which the needle is rotated in the direction indicated by the symbol "a"
Figure 13:
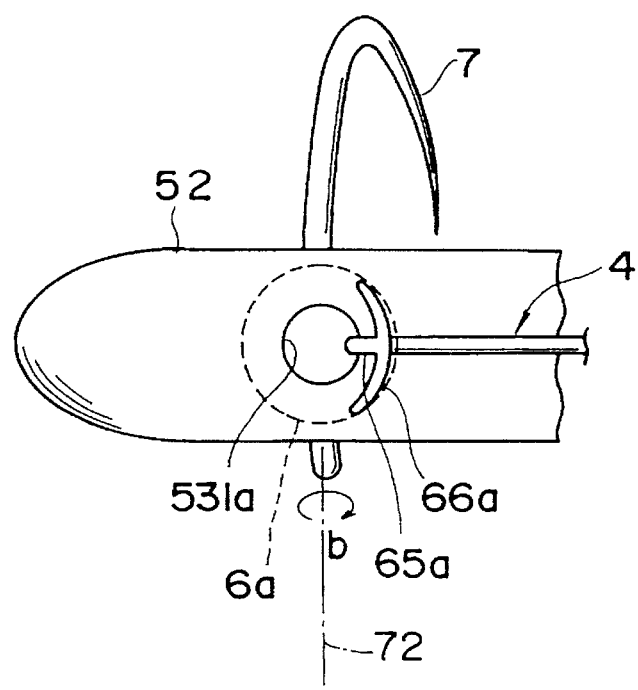
FIG. 13 is a top plan view of the tip of the needle holder, which shows the state in which the needle is rotated in the direction indicated by the symbol "b"

Stated more concretely, the needle 7 may be positioned by moving the pins 65a, 65b so as to rotate about their corresponding axes (i.e., the path indicated by the symbol "a" in FIG. 11), as shown in FIG. 12, by moving the pins 65a, 65b so as to rotate about the axis 72 of the base portion of the needle 7 held by the pins 65a, 65b (i.e., the path indicated by the symbol "b" in FIG. 11), as shown in FIG. 13, by moving the pins 65a, 65b so as to rotate about the axis of the insertion rod 3 (i.e., the path indicated by the symbol "c" in FIG. 3), as shown in FIG. 3, or by moving the pins so as to rotate at the same time in the "a" and "b" directions, the "b" and "c" directions, the "c" and "a" directions, or the "a", "b" and "c" directions.

In other words, by pivoting the control rod 41 about the axis of the pins 65a, 65b, it is possible to move the needle 7 in the "a" direction; by moving the control rod 41 along its own axial direction, it is possible to move the needle 7 in the "b" direction; and by moving the control rod 41 in a path that runs parallel to the axial direction of the side pin 66a, it is possible to move the needle 7 in the "c" direction. Also, because it is possible to carry out these operations through control of the control end portion 43 positioned outside the body, the position of the needle 7 can be freely adjusted from the outside of the body.

As for the operations described above, they may be easily carried out by employing a position control means like the one shown in FIG. 10.

After the needle 7 has been adjusted to a desired position, the arm 56 is rotated to bring the fixing members 51, 52 together. Then, as shown in FIG. 4, the fixing members 51, 52 clamp down on the pinch members 6a, 6b housed within the accommodating portions 53a, 53b to lock the pinch members 6a, 6b in place.

Figure 14:
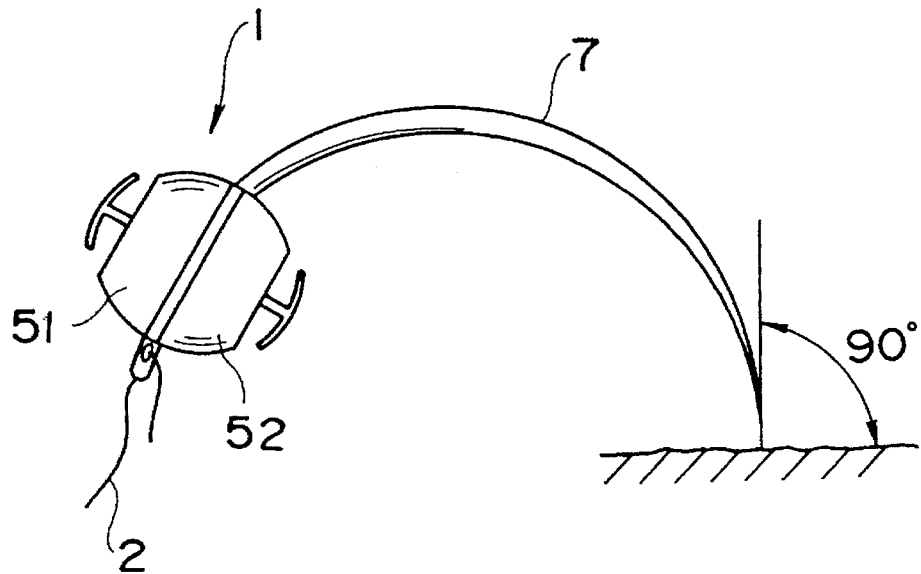
FIG. 14 illustrates a state in which a needle held by the needle holder according to the present invention is used to pierce tissue.

Next, by holding the handle port;ion 57 provided at the base end portion of the insertion rod 3, the needle holder 1 is manipulated, as shown in FIG. 14, to position the tip of the needle 7 at a right angle to the tissue that is to be sutured. Thereafter, by rotating the insertion rod 3 toward the tip of the needle 7, the tissue is pierced by the needle 7.

Figure 15:
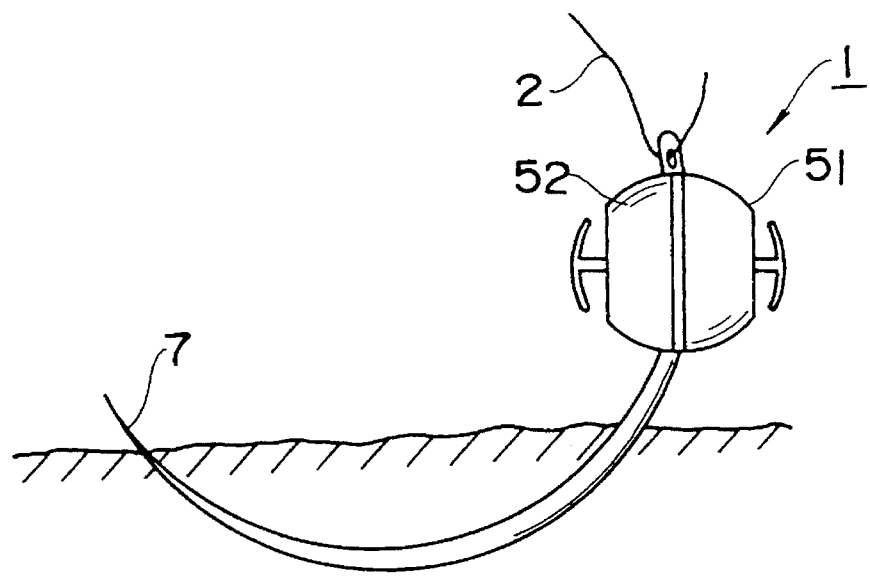
FIG. 15 illustrates the completed state of piercing tissue with a needle held by the needle holder according to the present invention.

Then, as shown in FIG. 15, as soon as the tip of the needle 7 comes out of the tissue being sutured, the piercing operation is completed.

Next, the arm 56 is rotated to enlarge the space between the fixing members 51, 52, and, as shown in FIG. 8, the fixing members 51, 52 are separated to force the edges of the holes 531a, 531b to engage with the side pins 66a, 66b to pull the pinch members 6a, 6b apart.

This then releases the grip on the needle 7 to enable the needle 7 to be easily pulled out of the needle holder 1 along the axial direction of the needle 7. At this time, as was previously stated, if a biasing member (spring) is provided at a position that is closer to the base end of the insertion rod 3 than the position of the needle 7, it becomes much easier to remove to the needle 7.

Then, by using forceps passed through a different trocar tube, the needle 7 is completely pulled through the tissue to pass the suturing thread 2 through the tissue. Finally, the thread 2 that has been passed through the tissue can be tied together.

The needle holder 1 according to the present invention is not limited to the embodiments described above. For example, instead of the pair of pinch members 6a, 6b used for holding the needle 7, it is possible to employ a magnetic means for holding the needle 7. Also, it is possible to hold the needle by utilizing an elastic holding means into which a needle can be passed and whose shape can be changed by applying a compressive force to an outside portion thereof to hold the needle securely. It is also possible to employ any other type of holding means.

Furthermore, when changing the position of the needle, the position changing directions of the needle need not be limited to three directions of motion or combinations thereof, and it is possible to move the needle in any one or two of the "a", "b" or "c" directions.

Moreover, the pinch members need not be limited to the half spherically shaped elements described above for the preferred embodiments. Instead, they may be replaced with a combination of rotational elements having rotational axes that are in different directions, preferably in orthogonal directions such as a joint cross. In other words, as long as rotation can be carried out in the directions described above, it is possible to employ any arrangement of elements.

Moreover, instead of the control rod described above, the position control means 4 may be constituted of a plurality of wires. Further, in the above embodiments, the insertion rod 3 is composed of the fixing members 51, 52 as the fixing means, these fixing members may be formed from separate parts. For example, it is possible to provide a pair of fixing members which can change a space therebetween like the fixing members 51, 52 described above, at a tip portion of an insertion rod.

Finally, it should be noted that the present invention is no limited to the embodiments described above, and the scope of the present invention is determined by the following claims.

What is claimed is:

1. A needle holder adapted to be passed from the outside of a body to the inside of a body cavity through a communicating tube to enable a needle to be inserted into the body cavity, comprising:

an elongated insertion rod having a tip portion;

holding means provided at the tip portion of the insertion rod for removably holding the needle, said holding means being rotatable in any direction with respect to the tip portion of said insertion rod;

position control means operatively associated with said holding means for adjusting the position of a needle to be held by said holding means by rotating said holding means, said position control means being operable from the outside of the body;

fixing means operatively associated with said holding means for fixing said holding means with respect to said insertion rod in a state in which said holding means has been adjusted by said position control means; and switching means operatively associated with said fixing means for switching the state of said holding means between a first state in which said holding means is adjustable with respect to said insertion rod through operation of said position control means and a second state in which said holding means is fixed with respect to said insertion rod by said fixing means.

2. The needle holder as claimed in claim 1, wherein said holding means comprises a pair of pinch members adapted for gripping the needle from two opposite sides.

3. The needle holder as claimed in claim 2, wherein each of said pair of pinch members has a substantially half spherical shape so that the pinch members form a roughly spherical shape when brought together.

4. The needle holder as claimed in claim 2, wherein said fixing means comprises a pair of fixing members adapted for clamping the pinch members from both sides thereof, and said switching means comprises a clamping mechanism for adjusting a clamping force applied by said fixing members to said pinch members.

5. The needle holder as claimed in claim 4, wherein each of the pair of pinch members has a half spherical shape so that the pinch members form a roughly spherical shape when brought together.

6. The needle holder as claimed in claim 5, wherein each of said fixing members has a roughly half spherical shaped concave portion between which is defined a space, and said pinch members are accommodated in the space defined by said concave portions of said fixing members.

7. The needle holder as claimed in claim 2, wherein said position control means is adapted to adjust the pinch members and the portion of the needle to be held by said pinch members by rotating said pinch members.

8. A needle holder adapted to be passed from the outside of a body to the inside of a body cavity through a communicating tube to enable a needle to be inserted into the body cavity, comprising:

an elongated insertion rod having a tip portion;

a pair of pinch members provided at the tip portion of said insertion rod for removably holding a needle, said pinch members being rotatable in any direction with respect to the tip portion of said insertion rod and being adapted to pinch therebetween a needle;

position control means operatively associated with said pinch members to rotate said pinch members and adjust the position of a needle held by said holding means, said position control means being operable from the outside of the body;

a pair of fixing members formed by at least a portion of said insertion rod, said fixing members being operatively associated with said pinch members to clamp said pinch members between said fixing members and thereby fix the position of the pinch members which has been adjusted by operation of said position control means; and switching means operatively associated with said fixing members for alternatively switching said pinch members between a first state in which said pinch members are adjustable through operation of said position control means and a second state in which said pinch members are fixed with respect to said insertion rod by said fixing members.

9. The needle holder as claimed in claim 8, wherein said switching means comprises a clamping mechanism for adjusting a clamping force applied by said fixing members to said pinch members.

10. The needle holder as claimed in claim 8, wherein each of the pinch members has a half spherical shape so that the pinch members form a roughly spherical shape when brought together.

11. The needle holder as claimed in claim 10, wherein each of said fixing members has a roughly half spherical shaped concave portion defining a space, and said pinch members are accommodated in the space defined by said concave portions of said fixing members.

12. A needle holder adapted to be passed from the outside of a body to the inside of a body cavity through a communicating tube to enable a needle to be inserted into the body cavity, comprising:

an elongated insertion rod having a tip portion;

a holder provided at the tip portion of the insertion rod for removably holding the needle, said holder being rotatable in any direction with respect to the tip portion of said insertion rod;

a pair of fixing members operatively associated with said holder to fix a position of said holder with respect to said insertion rod, said fixing members being movable with respect to one another to vary a distance between said fixing members;

a position controller operatively associated with said holder for adjusting a needle held by said holder through rotation of said holder, said position controller being operable from the outside of the body; and a switcher operatively associated with said fixing members to change the distance between the fixing members for switching a state of said holder between a first state in which said holder is adjustable with respect to said insertion rod through operation of said position controller and a second state in which said holder is fixed with respect to said insertion rod.

13. A needle holder adapted to be passed from the outside of a body to the inside of a body cavity through a communicating tube to enable a needle to be inserted into the body cavity, comprising:

an elongated insertion rod having a tip portion;

a holder provided at the tip portion of the insertion rod for removably holding the needle, said holder being rotatable about a plurality of different axes with respect to the tip portion of said insertion rod;

a fixing unit operatively associated with said holder to fix said holder with respect to said insertion rod;

a position controller operatively associated with said holder for adjusting the holder with respect to the insertion rod to thereby adjust a needle held by said holder, said position controller being operable from outside the body; and a switcher operatively associated with said fixing unit to switch the fixing unit between one position in which said holder is free to rotate with respect to the tip portion of the insertion rod to adjust a needle held by the holder and another position in which the holder is fixed with respect to the tip portion of the insertion rod to fix a needle held by said holder.

14. The needle holder as claimed in claim 13, wherein said holder includes pinch members each having an outer surface that is semi-spherical in shape.

15. The needle holder as claimed in claim 14, including a spring positioned between the pinch members to bias the pinch members away from one another.

16. The needle holder as claimed in claim 14, wherein said fixing unit includes a pair of fixing members.

17. The needle holder as claimed in claim 16, wherein each pinch member has a pin extending therefrom that extends through an opening in one of the fixing members.

* * * * *

UNITED STATES PATENT AND TRADEMARK OFFICE
CERTIFICATE OF CORRECTION

PATENT NO. : 5,556,402
DATED : September 17, 1996
INVENTOR(S) : Zhongren XU

It is certified that error appears in the above-indentified patent and that said Letters Patent is hereby corrected as shown below:

In column 4, line 16, delete "62*b*" and insert -- 61*b* --.

Signed and Sealed this

Seventh Day of January, 1997

Attest:

BRUCE LEHMAN

*Attesting Officer*          *Commissioner of Patents and Trademarks*